United States Patent [19]

Imrich et al.

[11] Patent Number: 5,415,994
[45] Date of Patent: May 16, 1995

[54] LATERAL FLOW MEDICAL DIAGNOSTIC ASSAY DEVICE WITH SAMPLE EXTRACTION MEANS

[75] Inventors: Michael R. Imrich, Encinitas; John K. Zeis, San Diego; Steven P. Miller, San Diego; Allan D. Pronovost, San Diego, all of Calif.

[73] Assignee: Quidel Corporation, San Diego, Calif.

[21] Appl. No.: 100,901

[22] Filed: Aug. 2, 1993

[51] Int. Cl.$^6$ .................. G01N 33/569; G01N 33/571
[52] U.S. Cl. ........................ 435/5; 435/7.32; 435/7.34; 435/7.36; 435/961; 435/970; 435/973; 435/975
[58] Field of Search ............... 435/7.32, 7.34, 7.36, 435/7.92, 7.94, 5, 29, 287, 961, 967, 970, 975, 973; 436/514, 518, 530, 531, 536, 538, 540, 174, 175, 808, 810; 422/50, 55, 57, 61, 101

[56] References Cited

U.S. PATENT DOCUMENTS

| | | | |
|---|---|---|---|
| Re. 33,850 | 3/1992 | Snyder et al. | 435/7.34 |
| 4,943,522 | 7/1990 | Eisinger et al. | 422/56 |
| 5,260,221 | 11/1993 | Ramel et al. | 422/56 |

OTHER PUBLICATIONS

Gosting et al., "Identification of a Species-Specific Antigen in *Legicnella pneumophila* by a Monoclonal Antibody", J. Clin. Microbiol., 20(c):1031–1035 (Dec. 1984).

Isenberg et al., "Indigenous and Pathogenic Microorganisms of Humans", pp. 24—35 in Manual of Clinical Microbiology, 4th Ed., (American Society for Microbiology, 1985).

Counts et al., "Evaluation of an Immunofluorescent-Antibody Test for Rapid Identification of *Pseudomonas aeruyimosa* in Blood Cultures", J. Clin. Microbiol., 26(6):1161–1165 (Jun. 1988).

*Primary Examiner*—Carol E. Bidwell
*Attorney, Agent, or Firm*—Townsend and Townsend Khourie and Crew

[57] ABSTRACT

The present invention provides devices, methods, and kits for treatment and detection of analytes requiring pretreatment in samples. One-step treatment and detection is possible utilizing the devices and methods of the present invention.

21 Claims, 4 Drawing Sheets

LATERAL FLOW MEDICAL DIAGNOSTIC ASSAY DEVICE WITH SAMPLE EXTRACTION MEANS

BACKGROUND OF THE INVENTION

The present invention provides devices, methods and kits for detecting analytes in biological samples. More particularly, the present invention provides means by which analytes requiring extraction from biological samples prior to detection may be extracted and detected in a single step.

Detection of analytes in biological samples has become an important aspect of medical practice. For example, identification and quantification of hormones in the blood can establish the diagnosis of many diseases, such as Cushing's disease or Syndrome of Inappropriate Antidiuretic Hormone. Also, recurrence of malignancies may often be determined by measurement of serum analytes such as carcinoembryonic antigen or prostate specific antigen. Generally, detection of such analytes requires complex instrumentation and assays are performed in reference laboratories.

Of particular value in clinical medicine is the detection of microbial pathogens in biological samples. As treatment may vary considerably depending upon the causative organism, accurate and rapid identification of pathogens in biological samples of patients suspected of having an infectious disease can be critical to provide prompt appropriate treatment to patients. Rapid identification of disease-causing organisms in biological samples is important even for non-life threatening infections. Traditionally, cultures were taken and empirical outpatient treatment begun. Often, patients receiving such empirical outpatient antibiotic treatment were lost to follow-up. This often occurs in syndromes such as pharyngitis or urethritis. After receiving antibiotics, the symptoms can improve even if the infectious organism is not eliminated. Therefore, as the symptoms improve the patient believes that they are cured while actually becoming chronically infected. Because the patient does not realize that they remain infected, they do not return to the physician for follow-up care based on the prior culture results. This may be detrimental to the patient as well as being a significant public health risk.

Traditionally, infectious diseases have been most commonly diagnosed by culture methods. Culturing microbial pathogens typically requires at least 24 hours to produce clinically relevant information. Rapid methods of diagnosing microbial infections have been developed to provide timely results for guiding clinical therapy. Some of the most effective of these rapid methods have been immunologically based. Monoclonal antibodies to microbe-specific antigens have been used to identify specific microbes in biological samples.

Group A Streptococcus in pharyngeal exudates can be identified by polyclonal or monoclonal antibodies to antigens specific for Group A Streptococcus. In their naturally occurring form, the Group A Streptococcus-specific antigens are not available for antibody binding and must be exposed prior to contacting with antibodies. This typically requires that the assay operator place the sample in acid and return later to transfer the acid solution to the assay medium. Multi-step assays such as these require more time and attention from health care personnel and thus are more expensive than one step assays.

Species-specific antigens of many other pathogenic organisms require pretreatment prior to detection. For example, *Legionella pneumophila* may be detected by non-serotype specific monoclonal antibodies after pretreatment with detergents and EDTA. Gosting et al., *J. Clin. Microbiol.*, 20:1031–1035 (1984). Porin F protein antigens of another significant human pathogen, *Pseudomonas aeruginosa*, also require treatment by detergents and EDTA in order to be optimally detected by monoclonal antibodies in clinical samples. Counts et al., *J. Clin. Microbiol.*, 26:1161–1165 (1988).

What is needed in the art are rapid means of detecting antigens which require pretreatment in biological samples. Preferably, these means are one step assays which minimize operator performance time. Quite surprisingly, the present invention fulfills these and other related needs.

SUMMARY OF THE INVENTION

The present invention provides devices, methods, and kits for one-step treatment and detection of analytes in samples. The devices of the present invention are particularly useful for the detection of analytes which require pretreatment to optimize detection. The devices are generally used to detect microbial antigens in biological samples.

The devices generally comprise an extraction chamber; a labelling zone having a means for specifically labelling the analyte; and a matrix defining an axial flow path in fluid connection with the extraction chamber, which matrix comprises a sample receiving zone and a capture zone located downstream from the sample receiving zone. The methods of detecting such analytes generally comprise inserting a swab containing the sample in the extraction chamber of a device as described above; inserting an extraction solution to the extraction chamber; observing accumulation of label in the capture zone of the device; and determining therefrom the presence or absence of the analyte in the sample. Kits comprising a device as described above and an extraction solution are also provided.

DESCRIPTION OF THE SPECIFIC EMBODIMENTS

Figure 1A:
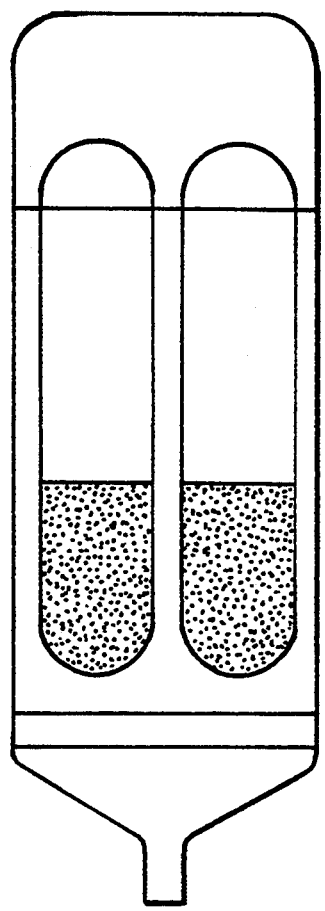
FIGS. 1A and 1B illustrate one embodiment of a multi-chambered allet that may be used in the methods of the present invention.

The present invention provides devices, methods, and kits for detecting the presence of an analyte in a sample. The present invention is particularly useful for detecting analytes which require pretreatment prior to detection. The present invention provides one step means to detect such pretreatment-requiring analytes. While the present invention is most commonly used to detect analytes which are specific for microbial pathogens in biological samples, other types of analytes may also be detected.

Generally, the samples will be biological material obtained or derived from patients. Physiological materials, such as urine, serum, cerebrospinal fluid, gastric secretions, nasal secretions, sputum, pharyngeal exudates, urethral or vaginal secretions, and the like may be assayed directly to detect the presence of analytes. Alternatively, when assaying tissue samples, the tissue will often require dissociation or liquification prior to insertion into devices of the present invention. In some instances it may be desirable to dilute the sample prior to performing the assay. Alternatively, analytes in the sample may be concentrated as by filtration or centrifugation.

Non-patient samples may also be assayed by devices and methods of the present invention. For example, microbial contamination of immortalized cell lines, food stuffs, agricultural products, and the like may be determined by the present invention. In some instances, analytes may also be identified in non-biological samples.

The devices and methods of the present invention provide a means for one-step pretreatment and detection of analytes. The analytes will generally be microbial antigens. These antigens may be detected on the surface of the microbial organism or may be solubilized from the organism during pretreatment. Other analytes which may be detected by the present invention include, e.g., monomeric constituents of polymeric protein chains which require dissociation prior to detection, protein bound analytes, and cancer-related antigens.

Generally, the devices and methods of the present invention employ lateral flow assay techniques as generally described in U.S. Pat. Nos. 4,943,522; 4,861,711; 4,857,453; 4,855,240; 4,775,636; 4,703,017; 4,361,537; 4,235,601; 4,168,146; 4,094,647; co-pending application U.S. patent application Ser. No. 07/639,967, European Patent Application Nos. 451,800; 158,746; 276,152; 306,772 and British Patent Application No. 2,204,398; each of which is incorporated herein by reference.

The devices of the present invention generally comprise an extraction chamber; a labelling zone having a means for specifically labelling the analyte; and a matrix which defines a flow path in fluid connection with the extraction chamber. A sample receiving zone and a capture zone are present on the matrix. The capture zone is located downstream from the sample receiving zone. By "downstream from the sample receiving zone", it is meant a location to which fluid applied to the sample receiving zone will flow.

The extraction chamber is generally located on the superior aspect of the device. The sample is placed in the chamber for pretreatment. Generally the sample will be present on a swab, wooden spatula, or other form of sample collecting apparatus. Alternatively, filters or other solid supports may hold the sample and be placed in the extraction chamber. The chamber has an sample administration port for introduction of the sample. The chamber also has an exit port through which the treated sample may flow to the sample receiving zone on the matrix. The size and shape of the extraction chamber are not critical and may vary. Typically, the extraction chamber has a distal cylindrical portion joined proximally to a bowl as demonstrated in FIGS. 2A and 2B. The cylindrical portion will often have a stop means to stop ingress of the sample containing support.

Following placement of the sample in the extraction chamber, an extraction solution may be added to the chamber which prepares the sample for detection. By "extraction solution", it is meant a solution comprising reagents which will treat the sample so that detection of the target analyte is enhanced. By "target analyte", it is meant the analyte of interest to be detected in the sample. For example, for the immunological detection of Group A streptococcus by devices of the present invention, a swab containing a sample of pharyngeal exudate may be pretreated with an acidic extraction solution, such as nitrous acid, to expose Group A streptococcus-specific antigens. Alternatively, to detect Legionella pneumophila by immunochemical means, a swab containing a sputum sample may be pretreated with an extraction solution containing a Triton X-100 detergent and EDTA in phosphate-buffered saline.

The extraction chamber is fluidly connected to the matrix by means of an exit port located distally in the chamber. The matrix defines a flow path for fluid flowing from the extraction chamber. The matrix of the assay device will typically be capable of non-bibulous lateral flow. By "non-bibulous lateral flow", it is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

A typical non-bibulous matrix material is the high density polyethylene sheet material such as manufactured by Porex Technologies Corp. of Fairburn, Ga., USA. This membrane has an open pore structure with a typical density, at 40% void volume, of 0.57 gm/cc and an average pore diameter of 1 to 250 micrometers, generally from 3 to 100 micrometers. The optimum pore diameter for the membrane for use in the invention is about 90 to about 140 $\mu$m. The membranes are from a few mils (0.001 in) to several mils in thickness, typically in the range of from 5 or 10 mils and up to 200 mils. The membrane is generally backed by a generally water impervious layer, but may be totally free standing. Other non-bibulous membranes, such as polyvinyl chloride, polyvinyl acetate, copolymers of vinyl acetate and vinyl chloride, polyamide, polycarbonate, nylon, glass fiber, orlon, polyester, polystyrene, and the like, or blends can also be used.

Bibulous materials, such as untreated paper, nitrocellulose, derivatized nylon, cellulose and the like may also be used following processing to provide non-bibulous flow. Blocking agents may block the forces which account for the bibulous nature of bibulous membranes. Suitable blocking agents include whole or derivatized bovine serum albumin or albumin from other animals, whole animal serum, casein, and non-fat dry milk.

The matrix comprises at least two zones, a sample receiving zone and a capture zone. The size and shape of the matrix are not critical and may vary. The matrix defines a lateral flow path. Generally, the matrix is rectangular and the flow path is axial.

Fluid from the extraction chamber contacts the matrix at the sample receiving zone. The sample receiving zone may contain a neutralizing agent which will neutralize the extraction solution prior to the assay. For example, sodium carbonate may be placed on the surface of the sample receiving zone to neutralize acidic extraction solutions such as employed to detect Group A streptococcus.

Generally, the labelling zone is present on the matrix flow path between the sample receiving zone and the capture zone. Alteratively, the labelling zone may be located in the exit port fluid connection between the extraction chamber and the sample receiving zone. The labelling zone contains a means for specifically labelling the target analyte. The labelling means will generally be a labelled immunoglobulin, such as an antibody, specific for the target analyte. The immunoglobulins may be antibodies of any isotype, such as IgE, IgG, or IgM, Fab fragments, F(ab')$_2$ fragments, Fab' fragments, or the like. Alternatively, the labelling means may be a non-immunoglobulin labelled compound which specifically binds the target analyte. For example, if the target analyte is a receptor molecule, the labelling means may be a labelled ligand for that receptor molecule. Hereinafter, the term "antibody" will be understood to refer to immunoglobulins and other substances which specifically bind target analytes.

The labels may be soluble or particulate and may include dyed immunoglobulin binding substances, simple dyes or dye polymers, dyed latex beads, dye-containing liposomes (such as described in U.S. Pat. No. 4,695,554, incorporated herein by reference), dyed cells or organisms, or metallic, organic, inorganic, or dye sols. The labels may be bound to the analyte-specific immunoglobulins by a variety of means which are well known in the art such as described in U.S. Pat. Nos. 4,863,875 and 4,373,932, each of which is incorporated herein by reference.

As the treated sample flows through the labelling zone, the target analyte in the sample binds the labelled antibody thereby indirectly labelling the target analyte. The sample continues to flow into the capture zone on the matrix. A compound capable of specifically binding the labelled target analyte is immobilized in the capture zone. Generally, target analyte-specific immunoglobulins will be immobilized in the capture zone. As the sample flows into the capture zone labelled target analytes will bind the immobilized immunoglobulins thereby retaining label in the capture zone. The presence of analyte in the sample may then be determined by visual identification of label retention in the capture zone.

The capture zone of devices of the present invention may include a procedure control line. The procedure control line is generally located downstream of the analyte specific binding compound immobilized in the capture zone. Retention of label by the procedural control line indicates that the sample has flowed through the capture zone and contacted the immobilized target specific binding substance.

The accumulation of visible label may be assessed either visually or by optical detection devices, such as reflectance analyzers, video image analyzers and the like. The accumulation of visible label can be assessed either to determine the presence or absence of label in the capture zone or the visible intensity of accumulated label which may then be correlated with the concentration or titer (dilution) of analyte in the patient sample (see, e.g., FIG. 6). The correlation between the visible intensity of accumulated label and analyte concentration may be made by comparison of the visible intensity to a reference standard. Optical detection devices may be programmed to automatically perform this comparison by means similar to that used by the Quidel Reflective Analyzer, Catalog No. QU0801 (Quidel Corp., San Diego, Calif.). Visual comparison is also possible by visual evaluation of the intensity and a color key such as used in the Quidel Total IgE Test Catalog No. 0701 (a multi-step ELISA assay). Thus, target analyte levels may be determined by devices of the present invention.

The devices of the present invention will often include an end-of-assay indicator to signal the test read time to the operator. The end-of-assay indicator is generally located on the matrix downstream from the capture zone.

A bibulous absorbent zone is generally included in the devices of the present invention. The absorbent zone is located downstream from the capture zone. The absorbent zone is a means for removing excess sample and unbound label from the matrix of the device. Generally, the absorbent zone will consist of an absorbent material such as filter paper, a glass fiber filter, or the like.

The end of assay indicator may consist of a pH indicating reagent (such as bromocresol green) impregnated in the absorbent zone. Upon contact with the treated sample, a pH change occurs in the processed absorbent. This pH shift converts the pH indicator to a different color (for instance, bromcresol green may be converted from yellow to blue) which is seen in an observation window over the absorbent zone. This technology may also serve as an internal assay control. For example, a neutralized extraction solution will convert the end of assay indicator from bright yellow to blue. If the neutralization is incomplete, the lower pH of the acidic sample solution will produce a green end color. An underneutralized sample may produce suspect results, the wrong color (green in this case) in the end of assay vent can serve as a signal that the assay may be comprised.

Alternatively, the end of assay may be constructed by applying a line of soluble ink on the capture zone (at the interface with the absorbent zone). The liquid front moving through the capture zone will solubilize the ink and transfer it into the absorbent. The resulting color change will be seen in an observation window above the absorbent zone, signifying end of assay.

In some embodiments of the present invention multiple analytes may be simultaneously detected from a single sample. In some of these embodiments, the several different target analytes may be labelled with visually distinctive labels and captured in different regions of a single capture zone. Alternatively, the sample receiving zone may be located upstream of a plurality of labelling zones and sample receiving zones which do not fluidly communicate with each other. Each labelling zone and associated capture zone detect a different analyte in the sample. In other embodiments, the extraction chamber may be fluidly connected to a plurality of sample receiving zones, each of which is located upstream of a labelling zone and capture zone for a different analyte.

Devices which simultaneously detect many different analytes have a variety of uses. For example, sputum samples of patients having respiratory infections may be evaluated for the presence of a variety of pathogens including *Mycoplasma pneumonia, Legionella pneumophila, Streptococcus pneumonia, Hemophilus influenza,* and *Moraxella catarrhalis.* Genital discharges may be assessed for the presence of *Chlamydia trachomatis, Neisseria gonorrhoeae, Mycoplasma pneumonia, Ureaplasma urealyticum,* and *Gardnerella vaginalis.* Thus, accurate diagnosis of common clinical syndromes may be rapidly obtained in an outpatient setting, even in mixed infections as frequently encountered in urethritis or vaginitis.

Conveniently, the matrix is contained within a solid casing. The extraction chamber is formed as an integral part of the top of the solid casing. An exit port fluidly connects the extraction chamber to the sample receiving zone of the matrix. The top surface of the solid casing generally has an observation window located over the capture zone of the matrix. In this embodiment, the sample may be placed in the extraction chamber and treated with the extraction solution to prepare the analyte for detection. The extraction solution will carry the treated analyte to the sample receiving zone on the matrix. Generally, the sample will flow through a labelling zone located on the matrix. Alternatively, the labelling zone may be a pad or filter located in the exit port flow path between the extraction chamber and matrix. The flow path of the matrix will guide the sample into the capture zone resulting in retention of labelled analyte present in the sample. Label retention may be detected through the observation window.

Injection molding, hand machine operations, cubital solder and stereolithographic techniques may be used to build plastic parts forming the solid casing. The device may be constructed of multiple plastic types including polystyrene, acrylic polymers, and urethane blends. Other non-plastic materials may also be used to form the solid casing.

Generally, there are two plastic components in the device. The top piece contains the sample processing features, the bottom piece is used for strip placement. The top and bottom components are constructed so that a press fit secures the assembly.

Filters may be placed in the extraction chamber between the sample and the exit port. The filters may act to remove particulate matter from the sample to improve flow kinetics on the matrix. The filters may also slow the egress of fluid from the extraction chamber to the matrix. This may prolong the treatment time of the analyte prior to the assay to maximize analyte availability.

The present invention also provides methods for detecting analytes in samples. The methods generally comprise inserting a swab into the extraction chamber of a device of the present invention; inserting an extraction solution into the extraction chamber; observing accumulation of label in the capture zone of the device; and determining therefrom the presence or absence of analyte in the sample.

The extraction solution mixes with the sample in the extraction chamber. The analyte is thereby pretreated and flows with the sample onto the matrix sample receiving zone. Analyte in the sample is contacted by the labelling means. Generally this will occur in a labelling zone on the matrix. The sample flows into the capture zone and labelled analyte is retained. Analyte in the sample is detected by observing accumulation of label as described above.

The present invention may also be performed in a competitive format. In one aspect, the labelling zone may contain labelled analyte in place of the labelled analyte binding substances. When the fluid sample contacts the labelling zone, the labelled analyte is mixed in the fluid and carried to the capture zone. The labelled analyte may then bind to an immobilized analyte binding substance in the capture zone. If the fluid sample contains target analytes (which have not been labelled), the labelled and unlabelled analytes will compete for binding to the analyte binding substance in the capture zone. If the fluid sample does not contain the target analyte, the labelled analyte will not be inhibited from binding with the analyte binding substance and the label color in the capture zone will be of maximum intensity. If unlabelled analyte is present in the fluid sample, some analyte binding substance will be bound by unlabelled analyte and the color intensity of the retained label will be decreased. The color intensity of the retained label will diminish as the concentration of analyte in the sample increases. The level of target analyte in a sample can then be determined by comparing the color intensity in the capture zone with predetermined reference standards as described above.

In another embodiment, labelled analyte may be bound to immobilized analyte binding substance in the capture zone. If target analyte is present in the sample, the labelled analyte will be displaced from the immobilized analyte binding substance and the color intensity of the capture zone will decrease as the fluid sample contacts the capture zone. The color change can be compared to reference standards to determine the level of target analyte in the sample.

As in the non-competitive format, any of the competitive formats may detect multiple analytes in a sample. The different analytes may be detected by means of different colored labels. In some embodiments, different capture zones will be employed for each different analyte to be detected. Alternatively, different analytes may be detected in a single capture zone if a combination of the different colored labels can be distinguished from the individual labels, as with a reflectance analyzer.

The present invention also provides kits for one-step treatment and detection of analytes in samples. The kits generally comprise a device of the claimed invention and a vial of the extraction solution. Often, a sample collecting apparatus, such as a swab or wood spatula, may be included in the kit. Color reference keys may also be included in the kits to facilitate determination of positive results or the level of an analyte in a sample.

The extraction solution may be contained in a single chamber vial or multi-chamber allet. Unstable extraction solutions may be mixed in the extraction chamber by insertion from a multi-chamber allet which contains the components of the solution. Upon mixing in the extraction chamber, the solution is activated and treats the analyte in the sample. Such solution mixing in the extraction chamber provides a means to enhance shelf-life of unstable solutions.

For example, nitrous acid is a relatively unstable solution. As a result, the reagents used to generate nitrous acid (for instance, sodium nitrite and acetic acid) must be mixed immediately before initiation of the antigen extraction process.

Figure 1B:
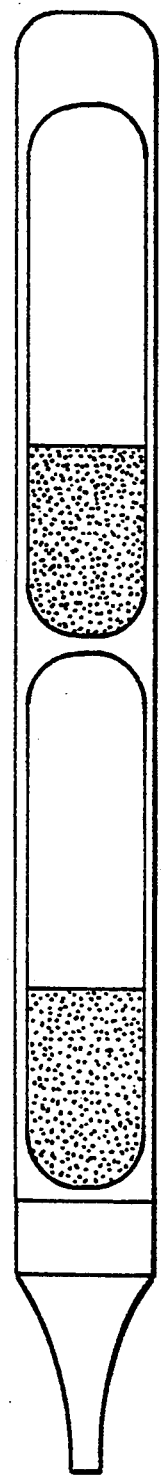

A system has been developed in which the liquid reagents are filled and sealed in crushable borosilicate glass ampules. The use of glass provides an effective barrier against vapor transmission and volume loss. The glass ampules may be configured in parallel or end to end. These ampules are encapsulated in a flexible tube, with a tip that allows the solution to be directed toward the target. See FIGS. 1A and 1B.

Nitrous acid is formed when the two ampules are broken, with the liquid contents allowed to mix. The ensuing extraction reagent can then be applied atop a swab in the extraction chamber.

Figure 2A:
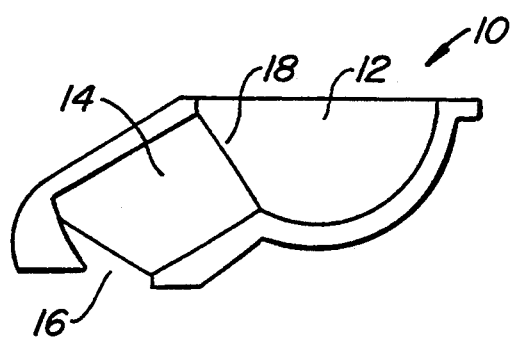
FIGS. 2A and 2B illustrate side and top views of one embodiment of an extraction chamber in a device of the present invention.
Figure 2B:
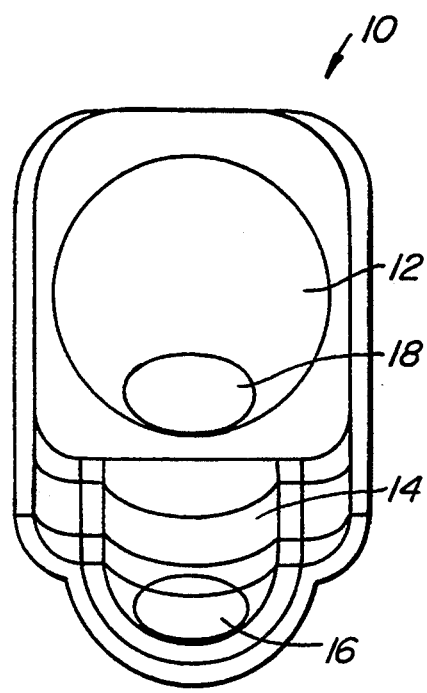

Referring now to the Figures, FIGS. 2A and 2B illustrate one embodiment of an extraction chamber 10 of the present invention. The illustrated extraction chamber 10 has a proximal bowl 12 and a distal cylindrical portion 14. The bowl 12 is joined to the cylindrical portion 14 by a circular opening 18. Samples on swabs are inserted into the cylindrical portion 14 through the bowl 12. After the sample-containing swab has been placed in the extraction chamber 10, the extraction solution may be added to the bowl 12 and then flow into the cylindrical portion 14. The treated sample may then flow through an exit port 16 located distally. The exit port 16 is located over the sample receiving zone of a matrix.

Figure 3:
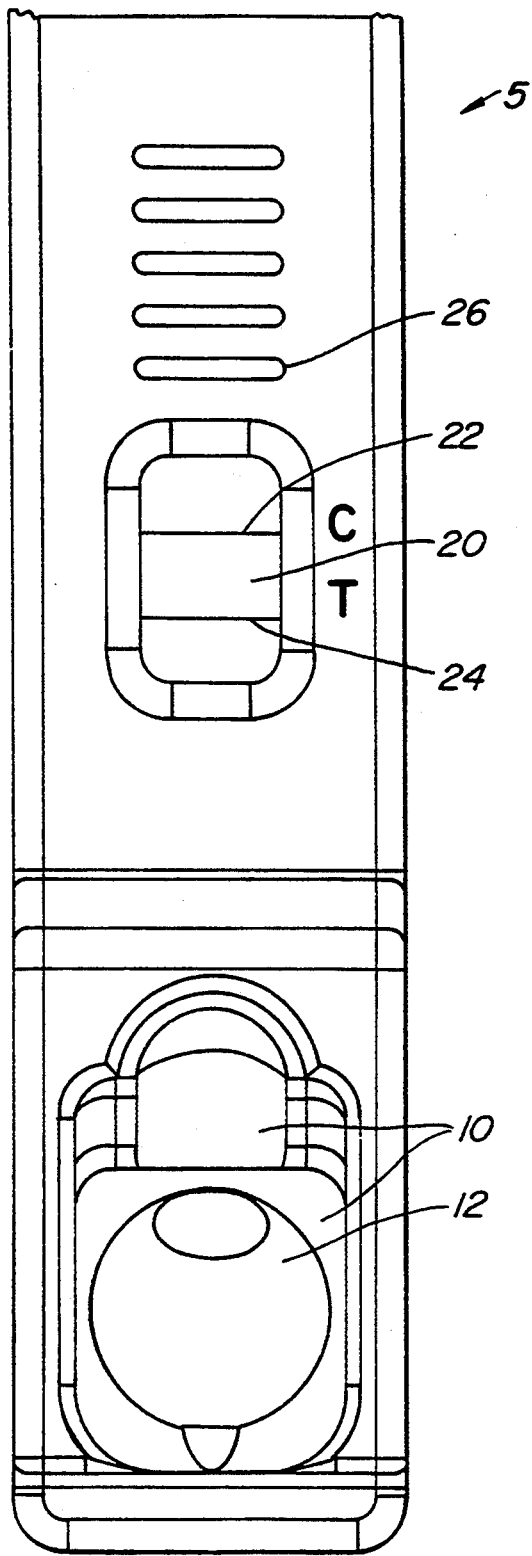
FIG. 3 illustrates a top view of a device of the present invention.

The superior aspect of a device 5 of the present invention is illustrated in FIG. 3. The device includes a top plate 7. An extraction chamber 10 is located on the top plate 7. An observation window 20 is located in the top plate 7 over the capture zone of the underlying matrix. The capture zone includes a test line 24 and a procedural control line 22. An end-of-assay indicator is located distal to the capture zone on the matrix. An end-of-assay window 26 is located in the top plate 7. Samples are introduced to the device in the extraction chamber 10. The samples are also treated with an extraction solution in the extraction chamber 10. The sample flows into the capture zone and bound analyte is detected on the test line 24. Accumulation of label on the procedural control capture line 22 indicates proper functioning of the device 5. The time to read the assay is indicated by the end-of-assay indicator observed through the end-of-assay window 26.

Figure 4:
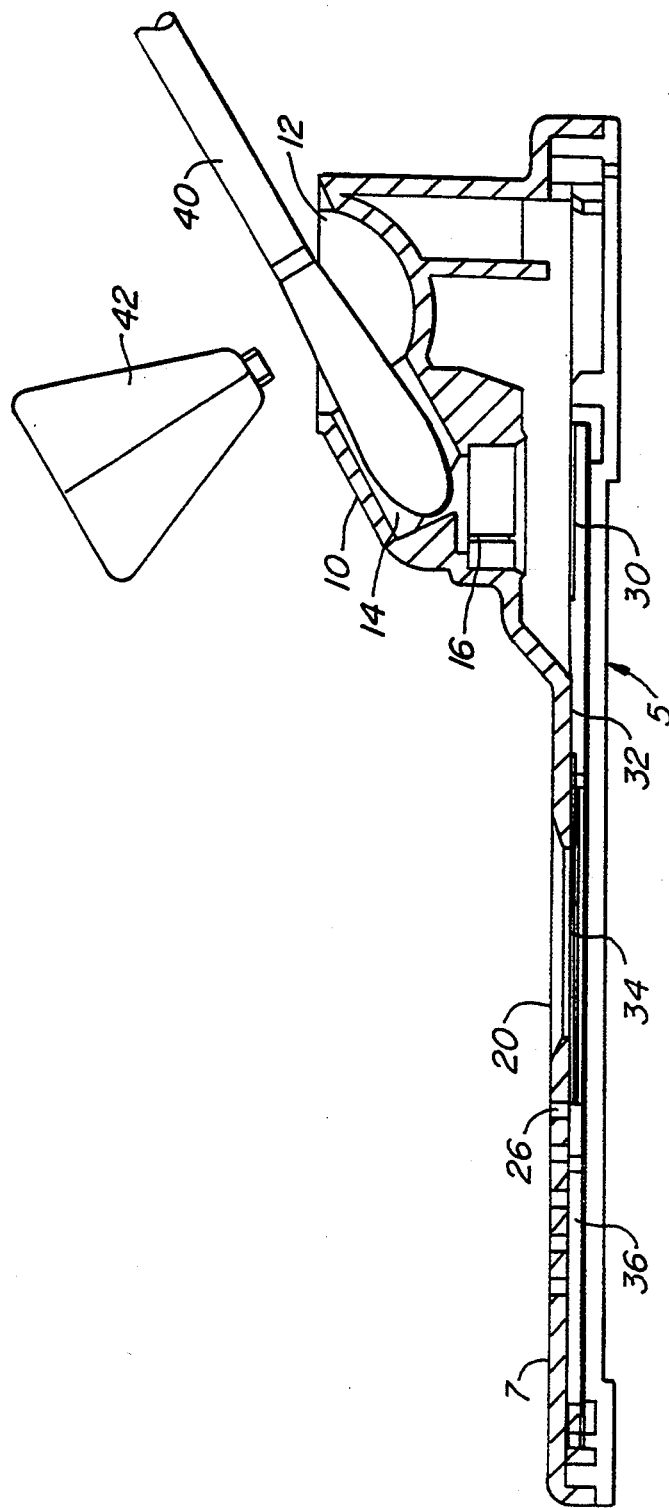
FIG. 4 illustrates a side view of a device of the present invention with a sample swab in the extraction chamber.

FIG. 4 illustrates a side view of a device 5 of the present invention. A sample-bearing swab 40 is positioned in the extraction chamber 10 for an assay of the sample. The extraction solution 42 is positioned to be applied to the sample. The swab has been inserted into the cylindrical portion 14 of the extraction chamber 10 through the bowl 12.

Following analyte extraction, the sample flows through the exit port 16 to the sample receiving zone 30 on the matrix. The sample flows through the labelling zone 32 on the matrix. Labelled analyte is captured in the capture zone 34. Excess sample is absorbed by the absorbent zone 36. The results of the assay may be observed through the observation window 20 of the top plate 7. Operators may identify the proper time at which to read the assay by observing a distinct color change, e.g., from yellow to blue, through the end-of-assay window 26.

Figure 5A:
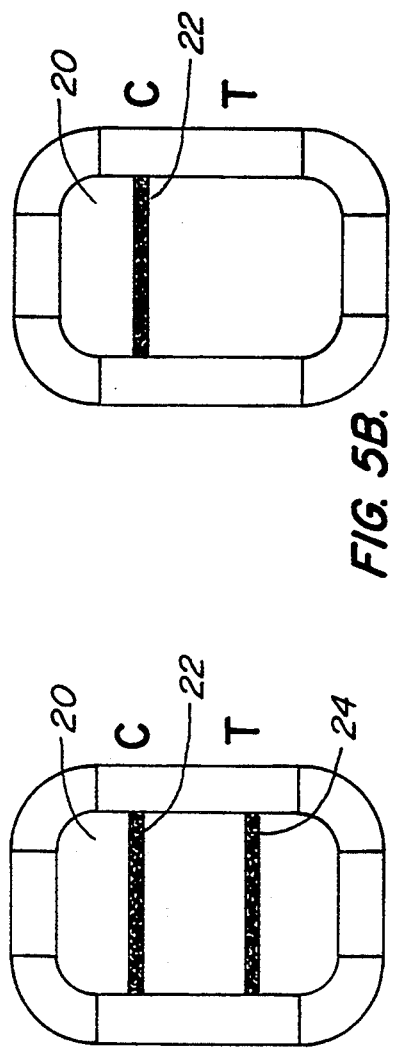
FIGS. 5A and 5B illustrate a positive and a negative result in a capture zone of a device of the present invention.
Figure 5B:
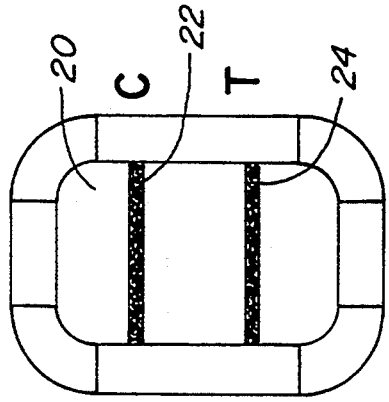

FIGS. 5A and 5B illustrate assay results in a device of the present invention having a procedural control line 20. The capture zones of the matrix are observed through observation window 20. FIG. 5A illustrates a positive result. Label has accumulated on both the test line 24 and the procedural control line 22. FIG. 5B illustrates a negative result. Label has accumulated only on the procedural control line 22 and no test line is apparent. If label does not accumulate on the procedural control line 22 during the assay, the device has malfunctioned and the assay results are suspect.

Figure 6:
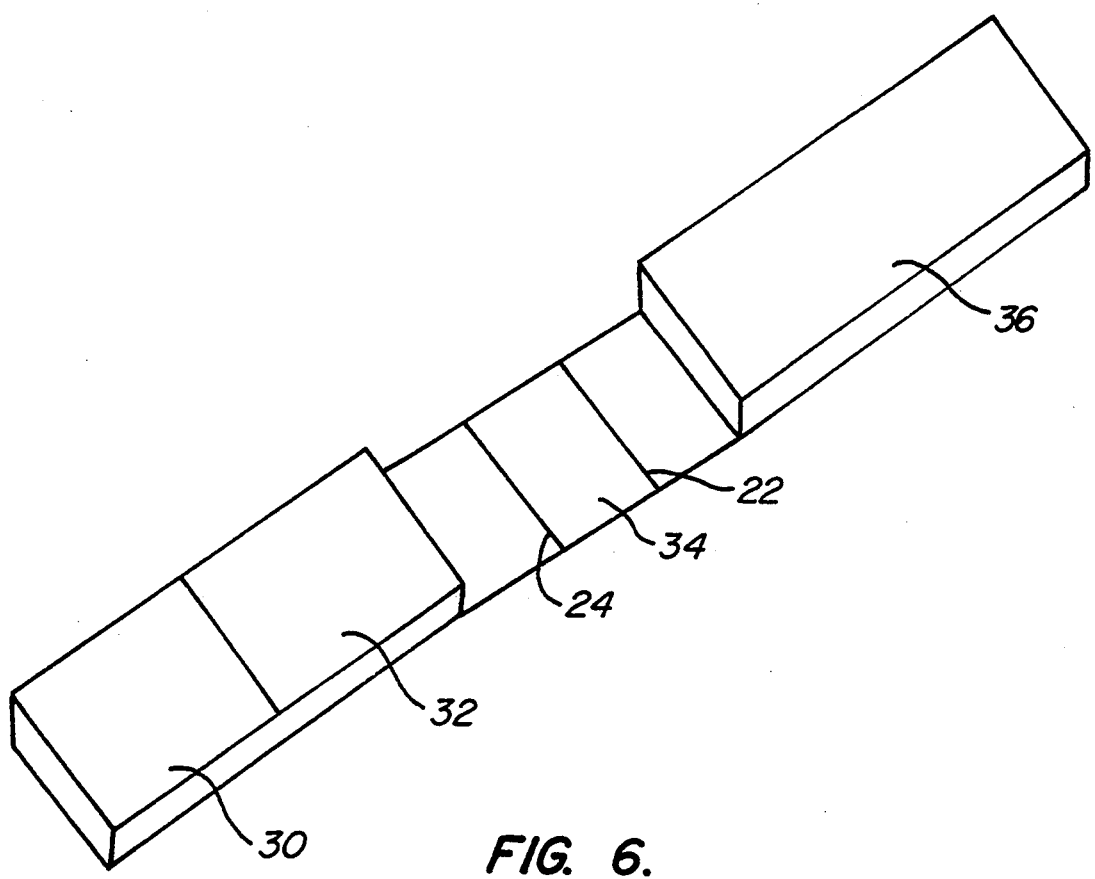
FIG. 6 illustrates a matrix having a sample receiving zone, a labelling zone, and a capture zone as used in some embodiments of devices of the present invention.

FIG. 6 illustrates a matrix for use in devices of the present invention. The matrix includes a sample receiving zone 30, a labelling zone, 32, a capture zone 34, and an absorbent zone 36. The capture zone 34 has a test line 24 and a procedural control line 22.

The following examples are offered by way of illustration, not by way of limitation.

EXAMPLES

Example 1—Preparation of a Device of the Present Invention

This example describes construction of a device of the present invention. The device was constructed to detect Group A streptococcus by means of a lateral flow assay. The device allowed one-step pretreatment and detection of Group A streptococcus organisms.

The sample receiving pad was prepared for incorporation into the matrix. Spunlaced acrylic, 1.2 oz. Sontara (DuPont) was backed with mylar using 3M adhesive 444. A 1M solution of sodium carbonate was applied to the backed Sontara at 38 $\mu l/cm^2$. The sodium carbonate is a base which will neutralize acid in the extraction solution prior to labelling or capturing the Group A streptococcal antigens. The inoculated Sontara was maintained on a level surface for 5 minutes to allow even dispersion of the solution. The inoculated Sontara was then placed in a 45° C. convection oven and dried for 16 hours. The resulting material was stored in a dry room <13% relative humidity (RH).

The labelling zone was then prepared. Mylar-backed Sontara as described above was suffused with a solution of Q-label specific for Group A Streptococcus and blue latex particles (Bangs) coated with Glucose Oxidase. The Q-Label was made with DEAE-Purified Rabbit anti-Strep A conjugated to Horseradish Peroxidase (Biozyme) that was subsequently "dyed" via reaction with 4-ChloroNaphthol (Sigma) and 3-methyl-2-benzothiazolinone hydrazone hydrochloride (MBTH) (Aldrich). The Q-Label and blue particles were diluted with a solution of modified BSA to a final Q-Label concentration of 1:6 for the Q-Label and 0.03% for the blue particles. This solution was applied to the mylar-backed Sontara at 38 $\mu l/cm^2$. Even dispersion of the solution was obtained by allowing the inoculated Sontara to remain on a level surface for 15 minutes following inoculation. The impregnated Sontara was freeze-dried in a Virtis freeze-dryer. The product was stored at <13% RH in a dry room.

The capture zone was prepared to contain a test line to identify Group A streptococcus antigens and a procedural control line. DEAE-Purified Rabbit anti-Strep A at 2 mg/ml in 50 mM Tris buffer, pH 8.0, was loaded into a pen compatible with the SE 780 X-Y Plotter (Asea Brown Boverti). A line of antibody solution was drawn upon a sheet of nitrocellulose (Schleicher and Schuell, 8 $\mu m$) with the instrument. Another pen was loaded with Sheep anti-Glucose Oxidase (Rockland), 2 mg/ml in a 10 mM phosphate buffer, pH 7.2, containing 150 mM sodium chloride (PBS) and a line of this solution was drawn parallel to the first line separated by 2 mm. Both lines were spotted at 0.5 sec/cm. The entire sheet of nitrocellulose was allowed to dry under ambient conditions for 10 minutes. Subsequently, the sheet was immersed in a solution of modified protein in 50 mM Tris-HCl buffer, pH 8.0, for 15 minutes to "block" any unbound sites on the nitrocellulose. The blocked membrane was blotted between two sheets of absorbent paper (Ahlstrom E-D 939-39) for 5 minutes, and then dried in a convection oven at 45° C. for 10 minutes. This capture membrane was backed with mylar coated with the 444 adhesive and stored in a dry room at <13% RH.

Test strips having one sample receiving zone, one labelling zone, and one capture zone were constructed from the individually prepared zones described above. The backed capture membrane, 2.1 cm, was adhered to mylar covered with the 444 adhesive. The sample receiving zone was applied, Sontara side up, 0.9 cm away and parallel to the capture zone. The labelling zone, 1.1 cm wide, was applied so that it bridged the 0.9 cm gap between the capture zone and the sample receiving zone. The labelling zone was applied so that the Sontara contacts the adhesive of the mylar backing and overlaps the capture and sample receiving zones by 1 mm. A 2 cm absorbent paper (Ahlstrom E-D 939-39) was adhered to the end of the strip opposite the sample receiving zone, with a 1 mm overlap on the capture zone (FIG. 5).

The test strip was then placed in a device of the present invention. A 0.29" disc of filter paper (Whatman #114) was inserted into the exit orifice of the extraction chamber. This flow regulator was secured and supported by insertion of a 0.295" disc of hydrophilic porous plastic (Porex #4744) which was press fit into place.

The test strip was centered in the bottom portion of the device. The top plate was aligned and snapped into place.

Example 2—Detection of Group A Streptococcus Organisms in a One-Step Assay

Assay devices as described above were used to perform assays on swabs spiked with decreasing amounts of killed Group A Streptococcus (Strep A) bacteria. A set of Strep A liquid calibrators (heat-inactivated Strep A quantitated via the McFarlane standard): $5\times10^8$, $5\times10^7$, and $5\times10^6$ bacteria/ml, was prepared. The inactivated bacteria were diluted in PBS containing 0.5% BSA. Ten microliters of calibrator was applied to a rayon-tipped solid shaft swab (Hardwood Products) to yield the following set of standards: $5\times10^6$, $5\times10^5$, $5\times10^4$ bacteria/test, as well as a negative sample (10 μl of PBS containing 0.5% BSA, spiked onto a swab).

The swab was inserted into the device, with its tip containing the "sample" in the extraction chamber. Nitrous acid solution, 375 μl (made from an equal volume of 1M sodium Nitrite and 1M Acetic Acid), was applied to the bowl of the extraction chamber. The swab was gently rotated a full revolution immediately after addition of the nitrous acid and a timer was started.

Figure 7:
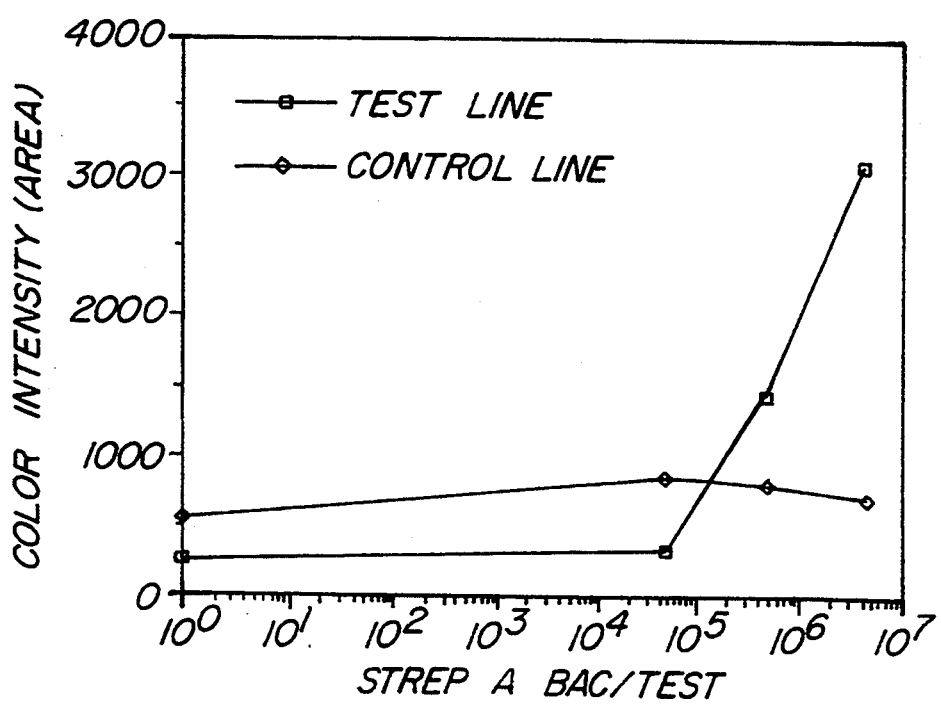
FIG. 7 illustrates a graph showing the color intensity of accumulated label in the capture zone of devices of the present invention with different concentrations of bacteria in test samples.

The point in time at which the red (test) and blue (control) lines first became visible was recorded. The strips were allowed to dry for two hours, and were then analyzed on the Videometric 150. FIG. 7 demonstrates the results. The intensity of the color signal increased rapidly with increasing bacterial load in the sample.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A device for detecting the presence of an analyte in a sample contained on a swab, said device comprising:
    an extraction chamber for extracting the analyte from the sample wherein the extraction chamber is disposed over a sample receiving zone on a matrix, and wherein the extraction chamber includes a bowl portion for receiving a liquid extraction solution and a cylindrical portion for receiving the swab; and
    a matrix having a sample receiving zone for receiving the extraction liquid containing the analyte, a labelling zone having means for specifically labelling the analyte as it passes therethrough and a capture zone having means for specifically binding the labelled analyte thereon, wherein the sample receiving zone, the labelling zone and the capture zone are arranged on the matrix in a liquid flow path.

2. The device of claim 1, wherein the labelling means is labelled immunoglobulin which specifically binds to the analyte.

3. The device of claim 1, wherein an immunoglobulin which specifically binds to the analyte is immobilized in the capture zone.

4. The device of claim 1 where the labelling means is labelled immunoglobulin that specifically binds to a microbial antigen.

5. The device as claimed in claim 4 wherein the labelled immunoglobulin is specific for the microbial antigen selected from the group consisting of Group A Streptococcus antigen, Group B Streptococcus antigen, *Pseudomonas aeruginosa* antigen, *Chlamydia trachomatis* antigen, *Neisseria gonorrhoeae* antigen, *Legionella pneumophila* antigen, and herpes simplex virus antigen.

6. The device of claim 1, wherein the matrix is a non-bibulous flow membrane.

7. The device of claim 1, further comprising an absorbent zone located downstream from the capture zone in the matrix.

8. A kit for the detection of an analyte in a sample, comprising:
    the device of claim 1; and
    a vial containing extraction reagents.

9. The kit of claim 8, wherein the vial is a multichamber allet.

10. A device for simultaneously detecting the presence of a plurality of analytes in a sample contained on a swab, said device comprising:
    an extraction chamber for extracting the analyte from the sample wherein the extraction chamber is disposed over a sample receiving zone on a matrix, and wherein the extraction chamber includes a bowl portion for receiving a liquid extraction solution and a cylindrical portion for receiving the swab; and
    a matrix having a sample receiving zone for receiving the extraction liquid containing the analyte, a labelling zone having means for specifically labelling each of the analytes as they pass therethrough and at least one capture zone having means for specifically binding a first labelled analyte thereon and at least one capture zone for specifically binding a second labelled analyte, wherein the sample receiving zone, the labelling zone and the capture zones are arranged on the matrix in a liquid flow path.

11. The device of claim 10, wherein an immunoglobulin which specifically binds to one analyte is immobilized in each capture zone.

12. The device of claim 10, wherein the matrix is a non-bibulous membrane.

13. The device of claim 10, wherein the immunoglobulin that specially binds to one analyte immobilized in each capture zone is specific for a microbial antigen.

14. The device of claim 13, wherein the immunoglobulin is specific for microbial antigen selected from the group consisting of *Chlamydia trachomatis* antigen, *Neisseria gonorrhoeae* antigen, *Mycoplasma pneumoniae* antigen, *Ureaplasma urealyticum* antigen and *Gardnerella vaginalis* antigen.

15. The device of claim 13, the immunoglobulin is specific for microbial antigen selected from the group consisting of *Mycoplasma pneumoniae* antigen, *Legionella pneumophila* antigen, *Streptococcus pneumoniae* antigen, *Hemophilus influenzae* antigen, and *Moraxella catarrhalis* antigen.

16. A method of detecting an analyte in a sample suspected of containing the analyte, comprising:

inserting a swab containing the sample into the cylindrical portion of the extraction chamber of the device of claim 1;

introducing an extraction solution into the bowl portion of the extraction chamber, wherein the analyte is extracted from the sample into the extraction solution and wherein the extraction solution containing the analyte is washed onto the receiving zone of the matrix and passes through the matrix of the device;

observing accumulation of label in the capture zone of the device; and determining therefrom the presence of the analyte in the sample by detecting the presence of the label in the capture zone.

17. The method of claim 16, wherein the extraction solution comprises an acid, a detergent or a chelator.

18. The method of claim 16, wherein the analyte is a microbial antigen.

19. A method of claim 18, wherein the microbial antigen is selected from the group consisting of Group A Streptococcus antigen, Group Streptococcus antigen, *Pseudomonas aeruginosa* antigen, *chlamydia trachomatis* antigen, *Neisseria gonorrhoea* antigen, *Legionella pneumophila* antigen, and herpes simplex virus antigen.

20. The method of claim 19, where the sample is a physiological fluid.

21. The method of claim 16, further comprising rotating the swab in the extraction solution.

* * * * *